United States Patent
Christians et al.

(10) Patent No.: US 9,051,611 B2
(45) Date of Patent: *Jun. 9, 2015

(54) MOLECULAR REDUNDANT SEQUENCING

(71) Applicant: Pacific Biosciences of California, Inc., Menlo Park, CA (US)

(72) Inventors: Fred Christians, Los Altos Hills, CA (US); Stephen Turner, Kirkland, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 13/967,070

(22) Filed: Aug. 14, 2013

(65) Prior Publication Data

US 2014/0017690 A1    Jan. 16, 2014

Related U.S. Application Data

(63) Continuation of application No. 13/020,634, filed on Feb. 3, 2011, now Pat. No. 8,535,882, which is a continuation of application No. 12/220,674, filed on Jul. 25, 2008, now Pat. No. 7,901,889.

(60) Provisional application No. 60/962,036, filed on Jul. 26, 2007.

(51) Int. Cl.
*C12Q 1/68* (2006.01)
*C07H 21/00* (2006.01)
*C07H 21/02* (2006.01)
*C07H 21/04* (2006.01)

(52) U.S. Cl.
CPC .................... *C12Q 1/6869* (2013.01)

(58) Field of Classification Search
CPC ........ C12Q 1/68; C12Q 1/6869; C07H 21/00; C07H 21/02; C07H 21/04
See application file for complete search history.

(56) References Cited

U.S. PATENT DOCUMENTS

| | | |
|---|---|---|
| 5,001,050 A | 3/1991 | Blanco et al. |
| 5,198,543 A | 3/1993 | Blanco et al. |
| 5,268,267 A | 12/1993 | Smith |
| 5,470,722 A | 11/1995 | Jones |
| 5,547,839 A | 8/1996 | Dower et al. |
| 5,576,204 A | 11/1996 | Blanco et al. |
| 5,648,245 A | 7/1997 | Fire et al. |
| 5,714,320 A | 2/1998 | Kool |
| 6,071,729 A | 6/2000 | Jeffries et al. |
| 6,210,896 B1 | 4/2001 | Chan |
| 6,255,083 B1 | 7/2001 | Williams |
| 6,261,808 B1 | 7/2001 | Auerbach |
| 6,312,913 B1 | 11/2001 | Wang et al. |
| 6,498,023 B1 | 12/2002 | Abarzua |
| 6,632,609 B2 | 10/2003 | Lizardi |
| 6,787,308 B2 | 9/2004 | Balasubramanian et al. |
| 7,056,661 B2 | 6/2006 | Korlach et al. |
| 7,170,050 B2 | 1/2007 | Turner et al. |
| 7,476,503 B2 | 1/2009 | Turner et al. |
| 7,981,604 B2 | 7/2011 | Quake |
| 2002/0012933 A1 | 1/2002 | Rothberg |
| 2002/0164629 A1 | 11/2002 | Quake et al. |
| 2002/0168645 A1 | 11/2002 | Taylor |
| 2003/0096253 A1 | 5/2003 | Nelson |
| 2003/0148988 A1 | 8/2003 | Kool |
| 2003/0190647 A1 | 10/2003 | Odera |
| 2003/0207267 A1 | 11/2003 | Lasken et al. |
| 2003/0215862 A1 | 11/2003 | Parce |
| 2003/0235849 A1 | 12/2003 | Lizardi et al. |
| 2004/0048300 A1 | 3/2004 | Sood et al. |
| 2004/0152119 A1 | 8/2004 | Sood et al. |
| 2004/0224319 A1 | 11/2004 | Sood et al. |
| 2004/0259082 A1 | 12/2004 | Williams |
| 2006/0024711 A1 | 2/2006 | Lapidus et al. |
| 2006/0046258 A1 | 3/2006 | Lapidus et al. |
| 2007/0141598 A1 | 6/2007 | Turner |
| 2008/0009007 A1 | 1/2008 | Lyle |
| 2008/0233575 A1 | 9/2008 | Harris et al. |
| 2009/0004666 A1 | 1/2009 | Tanabe et al. |
| 2009/0305248 A1 | 12/2009 | Lander et al. |

FOREIGN PATENT DOCUMENTS

| | | |
|---|---|---|
| JP | 2001510055 | 7/2001 |
| JP | 2002525049 T | 8/2002 |
| JP | 2002534123 | 10/2002 |
| JP | 2005512015 | 4/2005 |
| WO | 91/08678 | 5/1991 |
| WO | 96/27025 | 9/1996 |

(Continued)

OTHER PUBLICATIONS

Eid, et al., "Real-Time DNA Sequencing from Single Polymerase Molecules," Science (2009) 323:133-138.
Fire et al., "Rolling replication of short DNA circles" PNAS (1995) 92:4641-4645.
Levene et al., "Zero-mode waveguides for single molecule analysis at high concentrations" Science (2003) 229:682-686.
Orrego et al., "Determiniation of familial relationships" PCR Protocols: A guide to methods and applications, eds. Innis et al., Academic Press Inc., San Diego, CA (1990) Ch. 50.
Tsukamoto et al., "A highly polymorphic CA repeat marker at the human tumor necrosis factor alfa locus" J Hum Gen (1998) 43:278-279.
International Search Report and Written Opinion dated Feb. 23, 2009 for PCT/US2008/009064.
International Preliminary Report on Patentability dated Feb. 4, 2010 for PCT/US2008/009064.

(Continued)

*Primary Examiner* — Ethan Whisenant
(74) *Attorney, Agent, or Firm* — Deana A. Arnold (57) ABSTRACT

Methods, systems and compositions where a target nucleic acid includes a registration sequence disposed therein for identification of the number or relative position of determined sequence from the template sequence. Particularly preferred aspects include a registration sequence in a circular template nucleic acid sequence which is, in turn, used in sequence by incorporation processes that rely upon template dependent, polymerase mediated primer extension in the identification of the sequence of the template.

20 Claims, 4 Drawing Sheets

(56) References Cited

FOREIGN PATENT DOCUMENTS

| WO | 99/05315 | 2/1999 |
|---|---|---|
| WO | 99/07896 A2 | 2/1999 |
| WO | 0042195 | 7/2000 |
| WO | 0226934 | 4/2002 |
| WO | 03/074734 A2 | 9/2003 |

OTHER PUBLICATIONS

EP Extended Search Report dated Aug. 5, 2010 for EP 08780319.3

Bouck et al., "Analysis of the Quality and Utility of Random Shotgun Sequencing at Low Redundancies," Genome Research (1998) 8:1074-1084.

Cherry, J.M., "Computer Manipulations of DNA and Protein Sequences," Current Protocols in Molecular Biology (1995) 7.7.1-7.7.23.

Dean e al., "Rapid Amplification of Plasmid and Phage DNA Using Phi29 DNA Polymerase and Multiply-Primed Rolling Circle Amplification," Genome Research (2001) 11:1095.

Picard et al., "Use of Tuf Sequences for Genus-Specific PCR Detection and Phylogenetic Analysis of 28 *Streptococcal* Species," Journ of Clinical Microbiology (2004) 42(8):3586.

Smith et al., "Sequence and Topology of the CorA Magnesium Transport Systems of *Salmonella typhimurium* and *Escherichia coli*," J. of Biological Chemistry (1993) 268(19):14071-14080.

Fattah et al., "DNA Sequencing by the Tn3 Insertion in Vitro: Comparison of the Shotgun and Ordered Methods," Journ of Kansai Medical Univ. (2001) vol. 53(Nos. 1-4):135-140.

First Exam Report dated Jun. 27, 2011 for EP08780319.3.

First Office Action dated May 3, 2012 for related CN case 200880100371.X.

Second Office Action dated Jan. 14, 2013 for related CN case 200880100371.X.

Second Exam Report dated Feb. 4, 2013 for related EP08780319.3

Third Exam Report dated Apr. 26, 2013 for related EP08780319.3.

First Exam Report dated May 31, 2013 for related AU case 2008282862.

First Exam Report dated Jul. 29, 2013 for related JP case 20105181235.

Fourth Exam Report dated Dec. 6, 2013 for related EP08780319.3.

Second Exam Report dated Feb. 13, 2014 for related AU case 2008282862.

Fifth Exam Report dated Jun. 11, 2014 for related EP08780319.3.

First Exam Report dated Oct. 31, 2014 for related case CA 2,693,979.

Decision of Rejection dated Oct. 1, 2014 for related JP case 2010518235.

Polidoros et al., "Rolling Circle Amplification—RACE: A Method for Simultaneous Isolation of 5' nd 3' cDNA Ends From Amplified cDNA Templates," BioTechniques (2006) 41(1):35-40.

MOLECULAR REDUNDANT SEQUENCING

CROSS-REFERENCE TO RELATED APPLICATIONS

This application is a continuation of U.S. patent application Ser. No. 13/020,634 filed Feb. 3, 2011, which is a continuation of U.S. patent application Ser. No. 12/220,674 filed Jul. 25, 2008, which claims the benefit of Provisional Patent Application No. 60/962,036, filed Jul. 26, 2007, the full disclosures of which are incorporated herein by reference in their entirety for all purposes.

STATEMENT REGARDING FEDERALLY SPONSORED RESEARCH

Not Applicable.

BACKGROUND OF THE INVENTION

Genetic analysis is a key tool in biological research and is fast becoming an indispensable tool in the areas of pharmacology and even medical diagnostics. A wide variety of technologies, both old and new have been applied to such genetic analysis and particularly to the identification of nucleotide sequence analysis of larger fragments of genetic material.

However, as critical as raw genetic sequence data is in the overall analysis, by and large, it is analogous to a tring of letters used in a written novel. While the order of the letters is critical, it is their context within words, sentences, paragraphs and chapters that convey the lion's share of the information that is of most use. Similarly, while pure nucleotide sequence information is critically important in genetic analyses, it is the context of that sequence information in codons, genes, gene clusters, chromosomes and whole genomes that conveys even greater amounts of information.

In addition to sequence context, most common sequencing techniques are based upon analysis of populations of nucleic acids, and therefore derive sequence consensus from the bulk analysis of mixtures of nucleic acids. While this method is effective at getting an overall consensus sequence, it overlooks the variations from molecule to molecule that may be particularly important for a variety of different applications. In contrast, single molecule sequencing methods may suffer from inaccuracies that are not apparent in bulk consensus methods.

The present invention is generally directed to processes and systems that provide redundant sequence information on individual nucleic acid molecules that can be used in enhancing accuracy determinations as well as determining sequence context information in sequencing processes. These and other aspects of the invention are set forth in greater detail below.

BRIEF SUMMARY OF THE INVENTION

The present invention is generally directed to methods and systems for the repeated analysis of individual nucleic acid molecules so as to provide high accuracy sequence information from those individual molecules. In particular, the present invention provides improved methods, systems and compositions that are useful in performing redundant sequence analysis of individual polymers and particularly nucleic acid polymers.

In a first aspect, the invention provides methods of identifying a sequence context of a determined sequence of a target nucleic acid. The methods comprise providing a known registration sequence at a selected location in the target nucleic acid sequence, determining at least a portion of a sequence of the target nucleic acid including, the registration sequence, and identifying a sequence context of the portion of the sequence of the target nucleic acid determined in the determining step from a relative position of the registration sequence in the portion of the sequence.

In another aspect, the invention provides methods of sequencing a complete target nucleic acid, comprising providing a known registration sequence within the target nucleic acid sequence. The target nucleic acid is circularized and sequenced, using a sequencing process that is nondestructive to the target nucleic acid sequence until the registration sequence has been sequenced at least twice.

In still a further aspect, the invention provides methods of determining a nucleic acid sequence that comprise providing a template nucleic acid, a portion of which has at least a first sequence of nucleotides and a registration sequence at a selected location relative to the first sequence of nucleotides. The first sequence of nucleotides and the registration sequence are sequenced multiple times, and the sequence information from the sequencing step is aligned based at least in part upon the registration sequence identified in the sequencing step. A consensus sequence is then determined from the aligning step to determine the nucleic acid sequence of the first sequence of nucleotides.

In related aspects, the invention provides compositions for carrying out the foregoing methods. Such compositions typically include a nucleic acid synthesis complex that comprises a first template nucleic acid sequence that comprises at least a first exogenous registration sequence, a nucleic acid polymerase, and a primer sequence complementary to at least a portion of the first template nucleic acid sequence. The template nucleic acid sequence is configured for the nucleic acid polymerase to carry out a primer extension reaction over an identical sequence of nucleotides in the template nucleic acid sequence multiple times. The compositions also typically include a plurality of types of nucleotides or nucleotide analogs.

BRIEF DESCRIPTION OF THE DRAWINGS

FIG. 4A depicts a set of different length fragments (402, 404, 406) of a common sequence. FIG. 4B provides a schematic representation of sequence reads 422, 424 and 426. FIG. 4C illustrates the relative locations for sequences within the context of a template sequence.

DETAILED DESCRIPTION OF THE INVENTION

I. Generally

The present invention is generally directed to improved methods of determining sequence information for target nucleic acids, through the redundant sequencing of individual nucleic acid molecules. By repeatedly sequencing the same target sequence or portions thereof, one can dramatically improve the confidence in the sequence information that is derived from the process. The use of redundant sequence analysis in single molecule sequencing processes is described in published U.S. Patent Application No. 2006-0063264, the full disclosure of which is incorporated herein by reference for all purposes.

While the redundant sequencing processes described herein will find broad utility in a variety of sequencing processes, it will be appreciated that in particularly preferred aspects, these methods are employed in single molecule sequencing methods. Examples of single molecule methods are described in, e.g., U.S. Pat. Nos. 7,033,764, 7,052,847, 7,056,661, and 7,056,676, the full disclosures of which are incorporated herein by reference in their entirety for all purposes.

Briefly, a target or template nucleic acid is provided and configured so that a single molecule template dependent sequencing reaction will process an identical sequence of nucleotides in the sequence multiple times. Repeated sequencing of the identical sequence of nucleotides within the template improves the confidence level in the sequence information derived from that process, by providing redundant sequence analysis of the identical sequence of bases. By way of example, where there is a level of potential error associated with sequence identification or determination in a given sequencing process, a single pass over a given sequence will have that potential error as a limit on the confidence level of the sequence determined from that. Restated, if a sequencing process has a 10% error rate, one can only have a 90% confidence level in the determination of any base in that sequence. However, by repeatedly sequencing the identical sequence, one can systematically reduce the error level by comparing sequence information from each pass. Thus, for each pass, the error rate associated with the identification of a base from multiple passes, drops dramatically.

In addition to reduction of inherent inaccuracies in any sequencing process, redundant sequencing of individual nucleic acid molecules is of extremely high value in identifying genetic variation in low copy number environments, e.g., looking for intermolecular variation, which may not be identifiable from larger nucleic acid samples. For example, certain genetic anomalies may be present within a relatively small subset of cells in a given sample, or may be only a small subset of the genetic material within an individual cell. In such cases, sampling based upon broad selection of genetic material may wash out any distinction between the variant and normal material.

As will be appreciated from the instant disclosure, the methods of the invention may rely upon a number of configurations to accomplish the redundant sequence determination envisioned herein. Such configurations include the sequencing of multiple copies of a given sequence within an individual template molecule, redundant sequencing of the same set of nucleotides in a given template sequence by a single molecular complex, and sequencing of one or more identical sequences using multiple different molecular complexes, as well as combinations of these.

In addition to the process of redundant processing of nucleotide sequences, the present invention also provides improvements that facilitate such redundant sequencing, as well as methods for evaluating and processing redundant sequence data derived from these and related processes.

In addition to the foregoing, it is an object of the invention to provide the compositions that are described herein, including, for example, nucleic acid synthesis compositions that include the template sequences of the invention that include registration sequences in conjunction with nucleic acid polymerases and primer sequences and the plurality of types of nucleotides and/or nucleotide analogs for effecting primer extension and preferably, nucleic acid sequencing operations, e.g., using detectable analogs such as fluorescently labeled nucleotides or nucleotide analogs. Likewise, systems employing these compositions, and for carrying out these methods are also envisioned.

II. Redundant Sequences

As stated previously, the present invention provides for the redundant sequencing of a given sequence of nucleotides within a template sequence molecule multiple times. In accordance with the present invention, this redundant sequencing of a given sequence in a template molecule can employ a number of different configurations. For example, in at least one aspect, the sequence of nucleotides to be redundantly sequenced exists within a circular template molecule, and the sequencing process repeatedly processes around the circular template. As will be appreciated, where a circular template is employed, displacement of the nascent strand after the first revolution around the circle will permit continued or repetitive sequencing. In its simplest embodiment, this is accomplished through the use of strand displacing polymerase enzymes hi the sequencing process. A variety of strand displacing polymerases have been described, and particularly for use in sequencing by incorporation (See, e.g., International Patent Application Nos. WO 2007/075987; WO2007/075873; WO2007/076057, and their U.S. counterparts, the full disclosures of which are incorporated herein by reference in their entirety for all purposes. In brief, upon completion of a single revolution around the circular template, the polymerase will displace the newly synthesized nascent strand in order to continue synthesis around the template.

While use of strand displacing polymerases is the particularly preferred implementation of the invention as it relates to circular templates, a number of other methods may be employed to remove the nascent strand. For example, use of specific exonucleases to digest the open ended nascent strand can be employed to clear the nascent strand from the underlying template, while the synthesis process moves forward. In either case, where one is desirous of repeatedly sequencing the same set of nucleotides in a particular molecule, it will be appreciated that the process used for determining the sequence will be non-destructive to the template nucleic acid sequence. By way of example, digestive sequencing methods are not favored in these aspects. Similarly, sequencing methods that repeatedly require washing steps to de-protect and/or de-label incorporated and/or labeled nucleotides or terminator nucleotides tend to degrade the template strand after few cycles, and are thus not included in the methods of the invention where nondestructive sequence processes are employed.

In alternative aspects, the identical sequence of nucleotides, or target sequence, may be sequenced by providing multiple copies of such target sequence within a single template strand. As above, the template may be circular in order to provide additional layers of redundancy, or it may comprise a linear template. In using a linear template having multiple copies of the sequence of nucleotides, it will be appreciated that the identical sequence of nucleotides may be sequenced without the requirement of strand displacement or removal, as a single pass over the template will provide such redundant sequence reads. The linear template, in turn, can be prepared from a single originating template or target sequence, e.g., that is circularized and replicated through a rolling circle process, to provide a repeating pattern of the target sequence.

In still other aspects, a sequence of nucleotides may be repeatedly sequenced by reinitiating the priming of the template at a given priming site, and thus repeatedly sequencing the same portion of the template. Such re-initiation may, in its simplest form, comprise washing an immobilized template to remove a previous polymerization complex, and re-introducing a fresh polymerase primer mixture, to re-start the synthesis, and thus the sequencing process. Washing an immobilized template may comprise adjusting one or more of the temperature, pH and/or salt concentration of the reaction mixture to allow dissociation of the polymerase from the template. Likewise, a polymerase may simply be permitted to complete the sequencing of a single template molecule, by synthesizing off the end of a linear template. Following this, removal of the nascent/primer strand may be accomplished by adjusting the hybridization conditions, e.g., increasing the temperatures and/or salt concentration to melt the nascent strand from the template.

In still other aspects, multiple adjacently disposed polymerases, e.g., on adjacent, but optically resolvable portions of a substrate, e.g., a microscope slide or adjacent zero mode waveguides in a ZMW array, may be primed against different portions of the same template, so that they will repeatedly process, and thus sequence, the same portions of the template multiple times.

III. Sequencing Context

As noted above, the comparison or overlaying of sequence information derived from a molecular redundant sequence provides the advantages of increasing confidence in the sequence information obtained, by providing consensus identification of each base in the sequence of a given molecule. In facilitating that comparison, the context of the various pieces of sequence information is of great value. To that end, the present invention provides for and employs registration sequences within the template sequence in order to provide such context.

In at least one embodiment of the invention, the template sequence is provided with a registration sequence that indicates the context of the ensuing or preceding sequence in the template. For example, by providing a registration sequence at the beginning of each stretch of identical nucleotides in a sequence, one can readily identify the start of such sequence. In the case of circular templates, a registration sequence provides a set point on the template, and an indication of on the circular sequence the process is at a given time. In particular, by including in such sequence determination a sequence context parameter. The sequence context parameter facilitates the identification of the placement of a determined sequence fragment within the broader context of the overall target nucleic acid sequence or an even larger sequence region. In accordance with the present invention, the sequence context parameter comprises a registration sequence embedded within the target sequence. Inclusion of a registration sequence in a template provides an internal marker of a given location within the template sequence. Such a marker can provide benefits of permitting alignment of overlapping sequence reads from a given template molecule or from multiple copies of a template sequence, where the registration sequence is identically located within such multiple copies of the template sequence. Additionally, such registration sequences can provide markers of a given, relative location within a circular template molecule, providing an indication of completion of replication and/or sequencing of the circular template.

The registration sequences of the present invention are particularly useful in the context of sequencing by incorporation methods that have been or are being developed, and particularly those methods that rely upon sequence determination from individual template molecules. Sequencing by incorporation methods typically identify the bases in a sequence, based upon their order of incorporation in a template directed primer extension reaction. In particular, a base that is incorporated into a primer extension product is identified, and by complementarity, identifies the base in the template with which it is paired. Such sequencing methods include those that add bases in a stepwise fashion, in a template dependent primer extension reaction, where the base incorporated at each incorporation event is identified.

Typically, such methods utilize a dye labeled nucleotide that is capped or otherwise blocked, e.g., at the 3' hydroxyl group of the added base, to prevent further primer extension beyond that incorporation event. Once incorporated, the dye on the base is detected as an indication that the particular base was incorporated. The complex is then treated to remove the blocking or capping group and dye or label group, and the process is repeated to identify subsequent bases that will be incorporated, and thus identify the sequence of the underlying, template. Different variations of this process may interrogate the complex using a single type of base at a time, and identify whether that base is incorporated before trying a different base. Alternatively, they may use multiple, differently labeled bases simultaneously, and identify which base was incorporated from the spectral characteristics of the dye on the incorporated nucleotide. Still other methods employ non-fluorescent detection techniques that assess incorporation by assaying for the presence of an incorporation reaction by-product, e.g., pyrophosphate, using a luminescent enzymatic reporter system.

In particularly preferred aspects, the present invention is used in the context of real-time single molecule sequencing methods. Such methods are described, for example, in U.S. Pat. Nos. 7,033,764, 7,052,847, 7,056,661, and 7,056,676, the full disclosures of which are incorporated herein by reference for all purposes. Briefly, such methods typically provide a template/primer polymerase complex immobilized to a solid support such that an individual complex is optically resolvable from other complexes. Labeled nucleotides are introduced to the complex and their incorporation is directly observable. Direct observation may be supplied by the use of interactive labels, such as energy transfer donor/acceptor fluorophore pairs, where one of the donor or acceptor fluorophore is tethered proximal to the active site of the complex, e.g., on a separate location on the polymerase molecule, and the other member of the pair is attached to the nucleotide that is being incorporated. When the acceptor labeled nucleotide is incorporated, it is brought into proximity with the donor on the polymerase, and a detectable fluorescent signal is produced. Alternative strategies employ fluorophores that are, themselves, quenched until the cleavage of the polyphosphate chain from the nucleotide analog, during incorporation, which results in =quenching of the dye.

Still other preferred strategies provide for optical confinement of the immobilized complex such that incorporation brings a labeled nucleotide into the illumination/detection volume of the confinement for sufficient duration that the fluorescent label is detectable and distinguishable from randomly diffusing labels or labeled nucleotides (which have a more transient signal profile). Examples of particularly preferred confinements include arrays of zero mode waveguides. See, U.S. Pat. Nos. 7,033,764, 7,052,847, 7,056,661, and 7,056,676, previously incorporated herein by reference, and U.S. Pat. Nos. 6,991,726, 7,013,054, and 7,181,122, the full disclosures of which are incorporated herein by reference in their entirety for all purposes. In particular, such ZMWs are characterized by a cladding layer disposed over a transparent substrate, where the cladding layer has hollow cores disposed through it to the underlying substrate, and arrayed across the cladding/substrate. The provision of these cores having nanoscale cross sectional dimensions, e.g., from about 20 to about 200 nm in cross section in length, width or diameter), provides optical confinement within the core by attenuating propagation of light through the core, when the light is of a frequency that falls below a cut-off frequency for the core. As a result, light only penetrates a short distance into the core, providing a very small illumination volume at the end of the core from which the light is directed.

Figure 1:
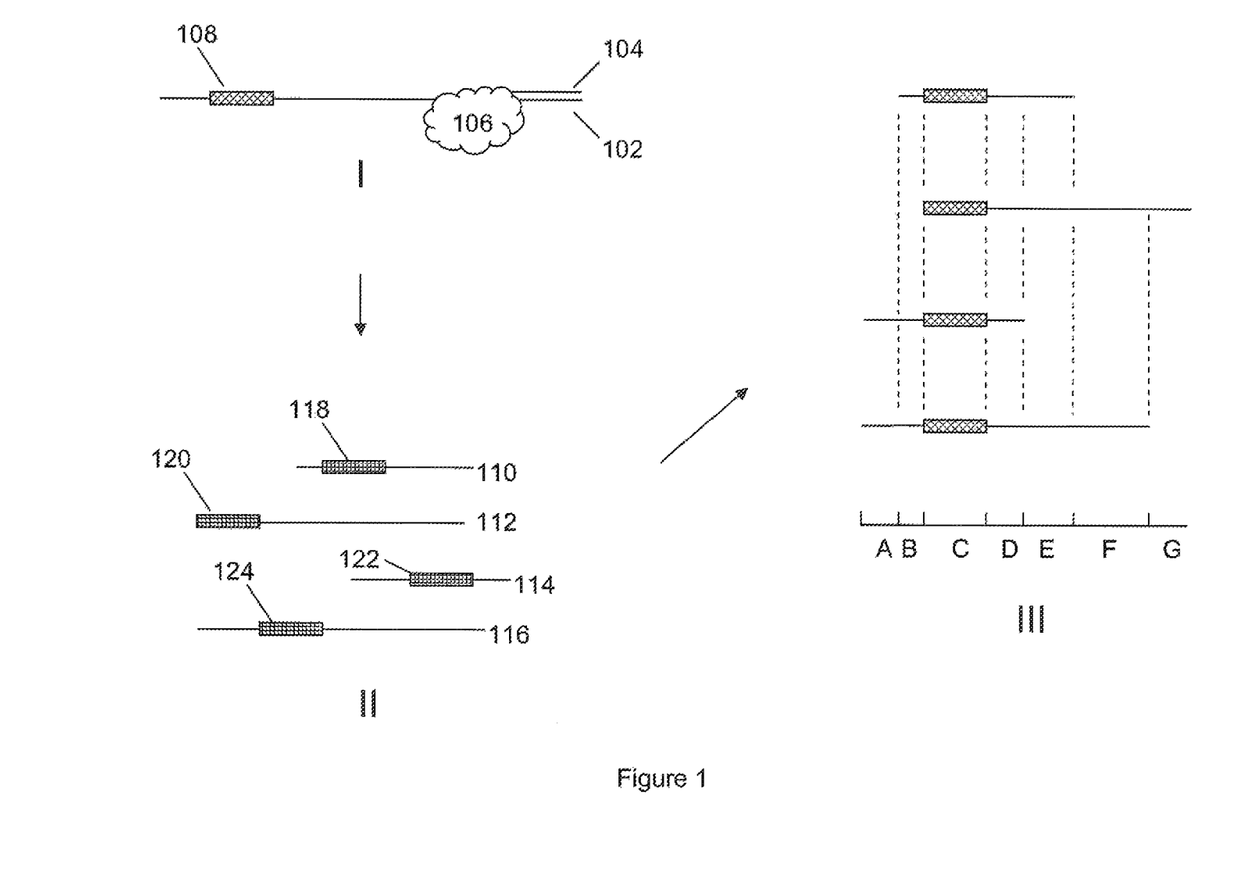
FIG. 1 schematically illustrates the methods of the invention in using registration sequences in the alignment of sequence information output from sequencing processes. Panel I depicts a primer extension reaction comprising a template molecule, a primer sequence, and a nucleic acid polymerase. Panel II illustrates sequences obtained from a target/template sequence in a primer extension reaction. Panel III shows alignment of such sequences.

As noted previously, the incorporation of registration sequences in the templates used for these sequencing methods provides reference or alignment sequences for sequence information that is obtained from the methods. Such alignment sequences may be used to identify repeated sections sequenced from circular templates or to align sequences obtained from the same or an identical set of linear or circular template sequences. FIG. 1 illustrates the use of such registration sequences in obtaining such alignment. In particular, as shown in panel I, a primer extension reaction is carried out upon a template molecule 102 having complexed thereto an appropriate primer sequence 104 and a nucleic acid polymerase 106. The template sequence 102 is provided with a registration sequence 108. The template may be a single template molecule that is iteratively reacted with a primer and polymerase enzyme in a primer extension reaction, e.g., as a linear molecule that is repeatedly reacted, or as a circular molecule that is subjected to continuous reaction, or it may comprise multiple identical template sequences reacted with one or more different polymerases and primers. Regardless of whether the template is a single molecule or multiple identical sequences; it includes a registration sequence (shown as the hatched box) at a certain location within that sequence.

As shown in panel II, from such template(s), the sequence information may be obtained that is somewhat disparate in nature, e.g., derived from different portions of the target/template sequence, such that repeated template directed primer extension by polymerase 106 yields sequence information or reads 110, 112, 114 and 116, that are derived from the template sequence, and which include the complement to registration sequence 108 (shown as registration complements 118, 120, 122 and 124, respectively.

By virtue of the presence of the registration sequence complements 118-124, one can determine how such determined sequences align, as shown in panel III. As noted elsewhere herein, this can provide an indication as to the extent of the sequence determination, e.g., if one has sequenced to a given point, or it can be used to determine the level of sequence coverage that has been obtained, in particular, in the context of nucleic acid sequencing, accuracy of the sequencing processes typically depends upon multifold sequencing or coverage of a given sequence region. By identifying the beginning and end of each pass over a given portion of a template sequence, one can readily determine the level of coverage from a single template molecule or portions thereof.

Likewise, in the context of sequencing multiple identical template molecules (or overlapping template molecules) in which the registration sequence is identically positioned in the context of the sequence, provides a measure of how many times one has sequenced the particular sequence region around the registration sequence. For example, with reference to FIG. 1, panel III, one can identify from the aligned sequences, that portions A and F of the sequence have been covered twice, portions B and E have been covered three times, and portions C (the registration sequence) and D have four-fold sequence coverage.

In some cases, it may be desirable to incorporate more than one registration sequence in a given template molecule, in order to bracket the sequence information that is obtained during a sequencing process. This allows for the identification of a beginning and ending point of a particular target sequence segment. Such multiple registration sequences in a given template may comprise the same or a different sequence of bases, to aid in their identification and distinction.

In other aspects, the registration sequences may be employed in separate fragments of genetic material for sequencing, with each fragment from a given region of a larger piece of genetic material, e.g., a genome, being tagged with a given registration sequence, while templates from different regions are tagged with different registration sequences. Sequencing of the registration sequence then provides for both the registration within the template of where the sequence process is, and an identification of where in the larger genomic context the particular fragment may have been derived from. In practice, one can divide larger genetic target material, e.g. a genome, into separate fractions, e.g. 100 kb, or 1 megabase, or a chromosome. The registration sequence is then added in multiple places within a fraction, e.g., by partial restriction digestion and ligation of the tag. In this way each piece within a given fraction gets the same registration sequence, which will serve as an identifying label, where all fractions are provided with a different registration sequence. All pieces from all fractions can then be pooled and sequenced. The registration sequence information is then used to assemble the individual reads; e.g., all reads with Registration Sequence 1 came from fraction 1, all reads with Registration Sequence 2 came from fraction 2. This fractionation is particularly helpful if there is repetitive sequence in the big target, so that the repeat can be assigned to its original location. Fractionation is also helpful in assembling short reads in large targets, a situation that makes assembly difficult.

As alluded to elsewhere herein, in addition to their use in alignment of sequence information, identification of the registration sequences within certain templates, e.g., circular templates or linear templates in which the registration sequence is positioned at the 5' terminus of the template, can provide an element confirmation that an entire template sequence has been sequenced, or that one has, at least sequenced through the 5' terminus of the template in question. In particular, with respect to circular templates, identification of the registration sequence appearing at least twice in sequencing the template provides confirmation that the entire sequence of the template has been interrogated/determined at a one-fold coverage. Further, as noted with respect to FIG. 1, above, such registration sequences can provide a direct readout of the level of sequence coverage from a single circular template or multiple identical templates.

Figure 2:
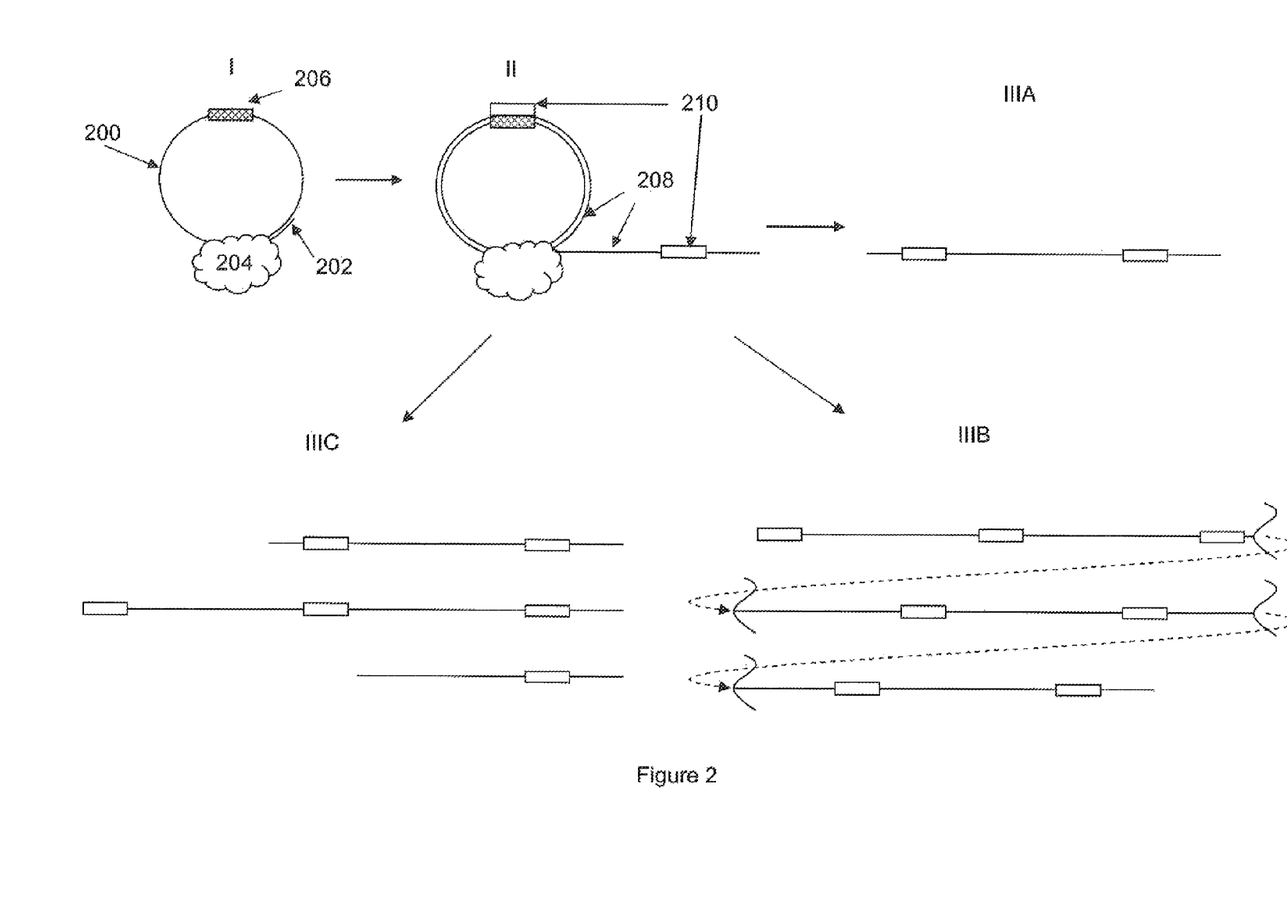
FIG. 2 schematically illustrates the methods of the invention applied to sequence information derived from circular template sequences. Panel I depicts a circular template molecule complexed with a primer sequence and a strand displacing polymerase. Panel II shows a primer extension reaction for the complex of panel I. Schematic representations of certain embodiments of sequence information obtained from the primer extension reaction are provided in panels IIIA, B, and C.

The foregoing is schematically illustrated in FIG. 2. As shown in panel I, a circular template molecule 200 is provided complexed with a primer sequence 202 and a strand displacing polymerase enzyme 204. The template sequence 200 includes a registration sequence portion 206. During the primer extension reaction (panel II), the extension reaction product 208 or nascent strand, is generated that includes the complementary sequence 210 to the registration sequence 206. The sequence information that is obtained from the reaction, e.g., using the preferred real time single molecule sequencing process is shown schematically in Panel IIIA, B and/or C. In particular, as shown in panel IIIA, one has obtained sequence information that spans from at least a first identification of the registration sequence 212 to a second identification of that sequence 214, with the sequence of the intervening segment 216 having been determined. As a result, one can readily ascertain that one has sequenced the entire circular template sequence at least one time. Multiple coverage sequencing is obtained by continually sequencing around the circular template, e.g., as shown in Panel IIIB. Determination of the level of coverage merely requires the number of passes over the intervening sequences between identifications of the registration sequence (shown is 6-fold coverage).

In still another aspect, sequence information obtained from multiple disparate extension reactions performed on the same circular template sequence, or multiple identical template sequences may be aligned and coordinated through the use of the registration sequence, as shown in Panel IIIC. For example, in some cases, discrete and noncontiguous pieces of sequence information may be obtained from primer extension from different portions of a circular template. This may be the result of interruption of a given primer extension reaction from polymerase dissociation, changes in reaction conditions, either intentional or otherwise, or multiple different extension reactions occurring on otherwise identical template sequences, where each different reaction provides an identifiable sequence output. These multiple discrete fragments of sequence information may then be correlated by virtue of their registration sequences, as shown in Panel IIIC.

Figure 3:
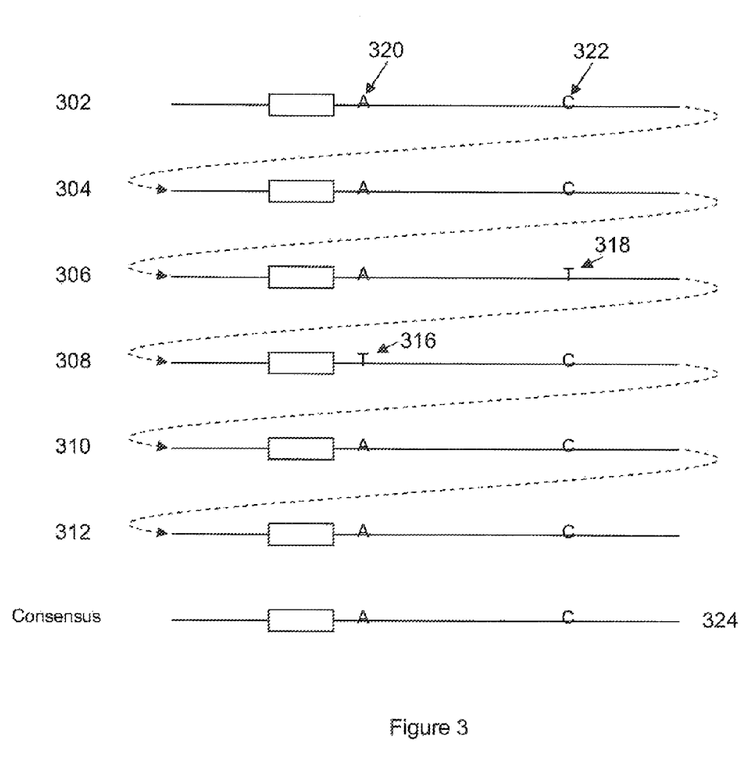
FIG. 3 schematically illustrates determination of consensus sequencing from the methods of the invention.

As noted previously, one can employ the registration sequences in obtaining consensus sequence information from a given template molecule. In particular, sequence information from a single template molecule in which identical sequences of nucleotides are repeatedly sequenced, is compared with itself by aligning the sequences, including, for example, aligning at least in part, based upon the identified registration sequences, and by multiplicative comparison, obtaining consensus sequence information for each base location in that sequence. An illustration of this consensus sequence determination is illustrated in FIG. 3. As shown, sequence reads from a single template in which an identical sequence of nucleotides is repeatedly sequenced (shown as sequences 302-312) are aligned based upon their registration sequence segments 314. As shown, the same sequences were derived from repeated sequencing of identical sequences within the same template, e.g., a circular template or repeated sequence template, as described elsewhere herein. Bases that are differently called in one or more sequence reads (e.g., bases 316 and 318) are compared against the consensus identification at the same location (e.g., bases 320 and 322). By obtaining sufficient consensus sequence information at a given sequence location, one can call with a desired level of confidence, the base at that location, and thus determine the consensus sequence 324 for the template.

As will be appreciated, the confidence with which one can call a base at a given location will depend upon the number of repeated sequence reads through the location, as well as the inherent error rate of the sequencing system employed. Notably, however, if one assumes a non-systematic error rate (e.g., rate of random sequence errors) of even as high as 25% during incorporation, it will be appreciated that five fold sequence coverage in a redundant sequencing process will yield a substantially lower error rate for a given sequence, e.g., theoretically lower than 0.1%.

In calling bases from redundant sequencing, it will be appreciated that a consensus for a given call must be established. Thus, to the extent that iterative sequencing at a given position results in ambiguity, e.g., it is identified differently in each sequencing pass, then a consensus call will require more than two calls at that position, in order to establish a majority consensus. Further, in order to increase confidence in such a consensus call, three, four, five, ten or more calls will need to be made at such position. By way of example, if a given position is identified once as an A, and once as a C, without more, it would be difficult to identify the correct base call at the position with any more than 50% accuracy. However, once additional calls are made at the position, e.g., 3 more A calls, then one can determine with reasonable certainty that the C call was incorrect.

Accordingly, in conjunction with the present invention, the comparison of sequence data from a given template comprises comparing at least 2 sequence reads from an identical set of nucleotide sequences in the template, preferably, at least 5 sequence reads, in some cases at least 10 sequence reads, and in still other cases, at least 15 sequences or even 20 sequence reads.

Once the multiple reads are obtained from a given target sequence, they are aligned and a consensus sequence is generated. In its simples form, the alignment may be accomplished manually by positioning the common sequence elements in the same sequence locations and adjusting for missing or substituted bases. In preferred aspects, however, alignment software is used to align the various sequence reads by computer. A variety of genetic alignment programs are readily available, including e.g., BLAST, FASTA, SSEARCH, SAM, DNABaser, and the like.

Again, once the various sequence reads are aligned, a consensus sequence may be established. In its simplest form, a simple majority call may be used to establish a consensus call for a given, position. However, in some cases, it will be desirable to establish a super majority for consensus base calls, in order to eliminate ambiguities that may derive from the error rates of the sequence process. For example, it may be desirable to require greater than a 51% majority to establish a consensus call, and in preferred aspects will require greater than a 60%, greater than 70%, greater than 75%, greater than 80% or even greater than 90% consensus in order to establish a consensus call at a given position. In preferred implementations, the sequence comparison and consensus base determination will again be done by computer that is appropriately programmed to receive the sequence data, and assign a consensus call based upon the percentage consensus for all of the aligned sequences.

III. Registration Sequences

The specific nature of the registration sequence will, at least in some part, depend upon the nature of the application to which that sequence is put. In particular, the length, and sequence make-up, and desired positioning (if any is desired) within the template sequence may be varied depending upon the application, as discussed in greater detail below. The known registration sequence is preferably an exogenously introduced registration sequence, also termed an "exogenous sequence" or the like, as contrasted to a known portion of the target nucleic acid sequence as, it exists in its original state. Such exogenous sequences will typically be preselected and introduced into thee target sequence during a sample preparation step, and in some cases designed, to provide optimal recognition of the registration sequence, based upon the nature of the template that is being sequenced, e.g., length, expected sequence context, likelihood of duplication of the registration sequence naturally within the template, etc. In addition to the preselection and/or design of an exogenous registration sequence, the registration sequence also is typically positioned within the target sequence at a certain location that may be selected. The selected location may be absolutely known, or known in a relative sense, e.g., known to exist a certain number of times, e.g., once, in a given template sequence, e.g., in a circular template, or positioned more proximal to or at the 3' or 5' terminus of a given template sequence.

The registration sequence may be selected to provide a maximum opportunity to definitively identify the registration sequence with a minimum probability of being duplicated within the target sequence. Typically, variation of the probability of non-duplication of a registration within the target sequence will be a function of the length of the registration sequence. As such, the length of the registration sequence within the target sequence will generally vary depending upon the length of the target sequence that is to be determined.

By way of example, the probability of a five base registration sequence otherwise existing within a random 1 kilobase target sequence, while not high, would be higher than the probability of a given 10 base sequence occurring in a 1 kilobase target sequence. As will be appreciated, the longer the template sequence, the longer will be the desired length of the registration sequence in order to account for the increased probability of duplication. Likewise, the greater the desire to avoid natural duplication within the template sequence, the longer will be the desired registration sequence. For purposes of most sequencing applications, e.g., real-time sequencing, where one will typically desire to sequence from 100 to 1000, 10,000 or more contiguous bases in a template sequence, the registration sequence will typically vary from about 5 to about 100 bases in length, or even longer, with preferred registration sequences being from about 10 to about 50 bases in length, or in some preferred aspects, from about 10 to about 20 bases in length.

The particular sequence of bases in the registration sequence is not a critical component, as the probability of any sequence of n bases existing in a larger sequence is the same regardless of the particular bases in that sequence. In some cases, however, it may be desirable to select the specific sequence of bases in the registration sequence, in order to take advantages of sequencing accuracy with respect to certain bases over others, readily identifiable dye combinations, expected sequence biases in the target sequence, or the like. Regardless of the identity of the bases in the target sequence, in accordance with the invention, the registration sequence is made up of a known sequence of bases, so that it may be readily identified from the target sequence in which it is embedded.

As noted above, the registration is typically provided at a certain selected relative location within the template sequence. By selected relative location is meant that the position of the registration sequence may not be definitively known, but that its position relative to some other component is selected at least in part. For example, in certain cases, e.g., linear target sequences, the registration sequence may be provided at or proximal to either of the 3' or 5' terminus of the target sequence.

In the case of circular sequences, however, the placement of the registration sequence anywhere within the circular target is considered a selected relative position, as its position, relative to itself (one full length of the target sequence away), is known.

Provision of the registration sequence within the target or template sequence may generally be accomplished by a variety of methods. For example, the registration sequence may be provided as an attached tag on a primer sequence used in replicating the target sequence, e.g., using PCR or other non-linear amplification processes, such that the target sequence exists substantially within the sample with the registration sequence disposed at either the 3' or 5' end of the strand that is to be sequenced. Ligation processes may also be used to append the registration sequence to one or the other terminus of one strand of a double stranded sequence. Subsequent melting of the double stranded template and complexing with the polymerase and primer, provides the newly synthesized template with the registration sequence included.

In at least one preferred aspect, a circular target nucleic acid is used as the template nucleic acid that is being sequenced, for example, as schematically illustrated in FIG. 2. In certain cases, such circular templates are particularly preferred for their ability to be repeatedly sequenced without the need for reinitiating complex formation. By repeatedly sequencing around the circular template, one can obtain sequence redundancy or multiple sequence coverage, and consequently, provide verification of the determined sequence. In using such redundant sequencing processes, however, it would be particularly useful to be able to recognize when the template has been sequenced completely or a given number of times. By including a registration sequence portion within the template, one can provide a built in counter for each time the circular template has been sequenced. In addition to providing confirmation that the circular template has been sequenced at least once, the registration also provides registration for alignment of multiple sequencings of the template to align the fold coverage. Such alignment may be provided for sequencing of a single circular molecule, or, in some cases, for multiple sequencings of identical circular template molecules, in which the registration sequence is provided at the same location in each template.

By way of example, in a sequencing by incorporation process, where one is using a circular template, one could not be certain that the entire template sequence had been obtained until there was sufficient sequence redundancy to indicate, at the desired level of probability, that the sequencing process had progressed around the circular template at least once. In working with de novo sequencing of a given template, because the correct sequence would be unknown, this would typically require several fold coverage of the overall template sequence before such a conclusion could be drawn. In employing a known registration sequence, one could ascertain that the sequence had been traversed at least once, at the point that the known registration sequence was traversed and identified twice, thus guarantying at least one complete trip around the circle. Further, in seeking multifold coverage, iterative identification of the registration within the sequence output from a single reaction would provide a direct indication of the level of sequence coverage one was obtaining from that template.

Creation of circular templates may be readily achieved using known sample preparation processes, whereby a registration sequence may be appended or ligated to a terminal portion of a linear template (or included as a tag on a pre-synthesized primer that is used in preparation of a template from an underlying target sequence), followed by circularization of the template, e.g., using circ ligase, or other known circularization techniques.

It will be appreciated that the registration sequence may exist as or as an integrated component of other sequence portions. For example, the registration sequence may operate as or be coupled to a sequencing primer recognition sequence. As such, the introduction of the registration sequence may be conducted concurrently with the introduction of the priming sequence. Other functional sequence components may include restriction sites, secondary structure inducing sequences, such as hair-pins, and the like.

While the present invention is generally described in terms of a real time read-out of the sequence information, it will be appreciated that preferred aspects will provide sequence data from sequencing portions or all of the template sequence followed by assessment of the sequence data with respect to the presence of the registration sequence. Identification of the transcribed registration sequence at least twice in the sequence data will provide an indication that the entire template sequence is provided in the readout.

Figure 4:
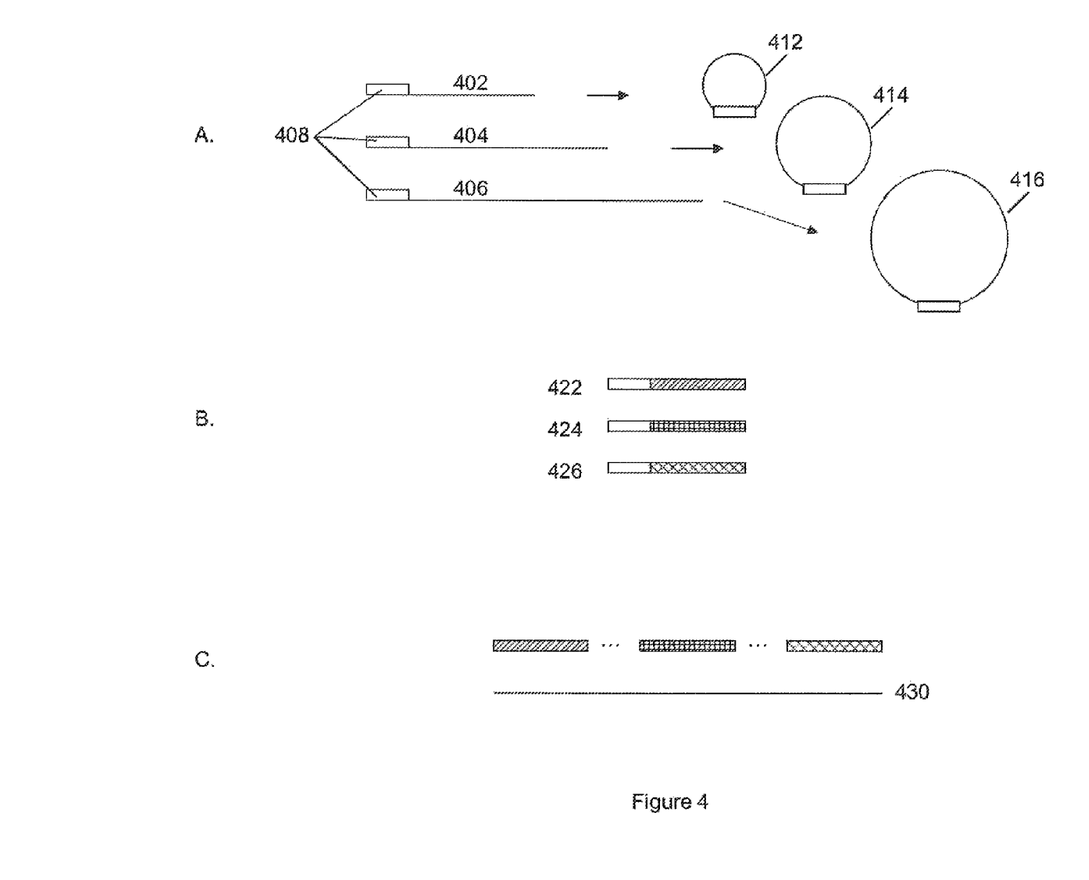
FIG. 4 schematically illustrates an alternative sequence context process using registration sequences.

Although described in terms of a fixed length template, it will also be appreciated that the registration sequences described herein may be included at one terminus of a varying length template which is then circularized. Doing so provides a differential readout from the registration sequence for segments of the template sequence that would be of varied distances from the registration sequence in the linear template, but which are placed adjacent the registration sequence when circularized. Providing a varying length template sequence may be accomplished through a variety of means, including, e.g., restriction or cleavage of the template sequence at varying points along its length, to create a nested set of fragments of the original template sequence, each having the registration sequence at one terminus and a different point in the overall sequence at the other terminus. When the template fragment is circularized, and sequenced in the direction from the registration sequence toward the newly ligated fragment terminus, one can obtain sequence context information from the new sequence, in conjunction with other determined sequences from other fragments of differing length. The result is to provide a virtual fold coverage of the template sequence through the sequencing of multiple nested template fragments. This is schematically illustrated in FIG. 4.

As shown in FIG. 4A, a set of different length fragments (402, 404, 406) of a common sequence are provided. A registration sequence 408 is coupled to the common end of the fragments, e.g., at the same sequence location, which are then circularized. The registration sequence is then used as an indication of a common starting point for the circular sequence, so that the uncommon regions adjacent the registration sequence are known to be coupled to but at varying distances from the common starting point. In particular, different length nested fragments (402, 404, 406) of a single template sequence are provided having a registration sequence 408 coupled to the common terminus of each of the fragments. Each fragment is then circularized to provide a circular template (e.g., circular templates 412, 414, 416). In sequencing across the registration sequence toward the uncommon end of the circularized fragment (as shown by the arrows), one can generate different sequence information from each of circular templates 412, 414 and 416 (shown schematically in FIG. 4B as sequence reads 422, 424 and 426, respectively).

Because each of these sequence reads is derived from the common underlying template, one knows that these fragments derive from a common sequence context. Further, by having knowledge of the relative lengths of the different fragments, e.g., by subjecting the fragments to a size based separation, one can provide relative locations for each of the uncommon sequences relative to each other, within the context of the overall template sequence. This is schematically illustrated in FIG. 4C. As shown, each determined sequence read is, by virtue of its origin from a particular sized fragment, able to be assigned a context within the underlying template sequence 430. Further, to the extent that any overlapping sequence portions exist within any two or more such sequence reads, one could determine a contiguous context for such reads.

What is claimed is:

1. A method of sequencing nucleic acid fragments within a genetic target material, comprising:
   fractionating the genetic target material into separate fractions;
   tagging each of said separate fractions with known exogenous registration sequences, wherein nucleic acid fragments in a single fraction are tagged with an identical known exogenous registration sequence and wherein nucleic acid fragments in said separate fractions are tagged with different known exogenous registration sequences: and further wherein the exogenous registration sequences provide identification of which separate fraction a given nucleic acid fragment was derived from, thereby generating tagged fragments in each of said separate fractions;
   circularizing the tagged fragments;
   pooling the tagged fragments from all of said separate fractions;
   sequencing the tagged fragments until the exogenous registration sequence has been sequenced at least twice, thereby generating sequence reads, each of which comprises at least two exogenous registration sequence portions and at least one tagged fragment sequence portion.

2. The method of claim 1, further comprising using said at least two exogenous registration sequence portions of each of said sequence reads to both (i) determine which of said separate fractions of the genetic target material corresponds to each of said tagged fragment sequence portions, and (ii) identify a sequence context of the tagged fragment sequence portion based on its position within a tagged fragment relative to the exogenous registration sequence portion.

3. The method of claim 1, wherein said sequencing is performed using a sequencing process that is nondestructive to the fragments sequence.

4. The method of claim 3, wherein said sequencing process comprises identifying bases upon incorporation in a template-directed, polymerase-mediated primer extension reaction, wherein the fragments comprise the template.

5. The method of claim 3, wherein said sequencing process comprises sequencing a product of rolling circle replication of the target nucleic acid sequence.

6. The method of claim 3, wherein said sequencing process comprises a Sanger sequencing process.

7. The method of claim 1, wherein the genetic target material is a genome.

8. The method of claim 7, wherein the separate fractions comprise fragments from different chromosomes of the genome.

9. A method of determining a nucleic acid sequence for a plurality of target nucleic acids, comprising:
   providing the plurality of target nucleic acids in separate fractions, wherein each of said separate fractions comprises a different subset of said target nucleic acids, wherein each different subset comprises target nucleic, acids from a genomic region of interest;
   tagging the target nucleic acids in the multiple separate fractions with exogenous registration sequences such that all of the target nucleic acids in a single fraction comprise the same exogenous registration sequence that is different from the exogenous registration sequences used to tag the target nucleic acids in other fractions, and further wherein said exogenous registration sequences tag said target nucleic acids at selected locations relative to a first sequence of nucleotides in said target nucleic acids;

sequencing the target nucleic acids to generate sequence reads comprising both target sequence information and exogenous registration sequence information such that the first sequence of nucleotides and registration sequence are sequenced multiple times;

aligning the sequence reads based at least in part upon the exogenous registration sequence information, thereby providing an aligned set of sequence reads for each of said separate fractions; and determining a consensus sequence from said aligned set of sequence reads to determine a nucleic acid sequence for each first sequence of nucleotides in each different subset of target nucleic acids.

10. The method of claim 9, wherein the target nucleic acids are circular nucleic acids.

11. The method of claim 9, wherein said sequencing is performed using a sequencing process that is nondestructive to the fragments sequence.

12. The method of claim 9, wherein said sequencing comprises sequencing the target nucleic acids at least five times.

13. The method of claim 9, wherein said aligning is performed by a computer.

14. A composition, comprising:
a set of nucleic acid synthesis complexes comprising:
  a set of circular nucleic acid templates comprising different length fragments of a nucleic acid region of interest, each having a common 5'-terminal sequence, wherein each of the circular nucleic acid templates comprises one of said different length fragments and one exogenous registration sequence, wherein the 5'-end of said fragment is linked to a 3'-end of the exogenous registration sequence, and the 3'-end of said fragment is linked to a 5'-end of the exogenous registration sequence;
  a primer sequence annealed to at least a portion of the exogenous registration sequence in each of said circular nucleic acid templates, and
  a nucleic acid polymerase bound to each of said circular nucleic acid templates at said primer sequence; and
a plurality of types of nucleotides or nucleotide analogs.

15. The composition of claim 14, wherein the plurality of types of nucleotides or nucleotide analogs comprise detectable labels.

16. A method of sequencing a nucleic acid region of interest, the method comprising:
providing a nucleic acid region of interest;
fragmenting the nucleic acid region of interest to produce a nested set of fragments of the nucleic acid region of interest, wherein the nested set comprises fragments of varying lengths, and further wherein each fragment in the nested set comprises a common 5'-terminal sequence and a variable 3'-terminal sequence, such that each terminates at a different point in the nucleic acid region of interest depending on its length;
circularizing each fragment in the nested set of fragments by linking a 3'-end of an exogenous registration sequence to the 5'-end of each fragment in the nested set and linking a 5'-end of the exogenous registration sequence to the 3'-end of each fragment in the nested set, thereby generating circular nucleic acid templates of varying sizes;
sequencing each of the circular nucleic acid templates, thereby generating sequence reads comprising sequence information for the variable 3'-terminal sequences; and
assembling the sequence reads based upon the sequence information for the variable terminal sequences and the varying sizes of the circular nucleic acid templates.

17. The method of claim 16, wherein said sequencing process comprises identifying bases during incorporation in a template-directed, polymerase-mediated primer extension reaction performed on the circular nucleic acid templates, wherein a polymerase synthesizes a nascent strand in a direction from the exogenous registration sequence toward the variable 5'-terminal sequences.

18. The method of claim 16, wherein a primer is annealed to the exogenous registration sequence prior to said sequencing.

19. The method of claim 16, further comprising subjecting the fragments in the nested set to a size-based separation prior to said circularizing.

20. The method of claim 16, wherein overlapping sequence portions exist between two or more of said sequence reads, and further wherein said assembling further comprises using said overlapping sequence portions.

* * * * *